(12) United States Patent
McNeary

(10) Patent No.: US 9,393,281 B2
(45) Date of Patent: Jul. 19, 2016

(54) COMPOSITION OF BETA-GLUCAN AND ASHWAGANDHA

(71) Applicant: Nutragenesis, LLC, Brattleboro, VT (US)

(72) Inventor: Peter S. McNeary, Brattleboro, VT (US)

(73) Assignees: Nutragenesis, LLC, Brattleboro, VT (US); Natreon, Inc., New Brunswick, NJ (US)

( * ) Notice: Subject to any disclaimer, the term of this patent is extended or adjusted under 35 U.S.C. 154(b) by 291 days.

(21) Appl. No.: 14/094,251

(22) Filed: Dec. 2, 2013

(65) Prior Publication Data
US 2014/0087009 A1    Mar. 27, 2014

Related U.S. Application Data

(62) Division of application No. 13/532,338, filed on Jun. 25, 2012, now Pat. No. 8,597,697.

(60) Provisional application No. 61/501,029, filed on Jun. 24, 2011.

(51) Int. Cl.
*A61K 36/00* (2006.01)
*A61K 45/00* (2006.01)
*A61K 36/81* (2006.01)
*A61K 31/716* (2006.01)

(52) U.S. Cl.
CPC ............ *A61K 36/81* (2013.01); *A61K 31/716* (2013.01)

(58) Field of Classification Search
None
See application file for complete search history.

(56) References Cited

U.S. PATENT DOCUMENTS

| | | | |
|---|---|---|---|
| 5,854,404 A | 12/1998 | Nanba et al. | |
| 6,124,268 A | 9/2000 | Ghosal | |
| 6,153,198 A | 11/2000 | Ghosal | |
| 6,290,996 B1 | 9/2001 | Ghosal | |
| 6,362,167 B1 | 3/2002 | Ghosal | |
| 6,713,092 B1 | 3/2004 | Ghosal | |
| 7,001,619 B2 | 2/2006 | Johri et al. | |
| 8,206,757 B2 | 6/2012 | McNeary | |
| 8,329,231 B2 | 12/2012 | McNeary | |
| 2006/0147561 A1 | 7/2006 | Pushpangadan et al. | |
| 2006/0172021 A1 | 8/2006 | Moffett | |
| 2007/0196381 A1 | 8/2007 | Holt | |
| 2008/0261916 A1 | 10/2008 | Jaszberenyi et al. | |
| 2010/0015109 A1 | 1/2010 | Bias | |
| 2010/0098785 A1 | 4/2010 | McNeary | |
| 2012/0288574 A1 | 11/2012 | McNeary | |
| 2012/0328663 A1 | 12/2012 | McNeary | |

FOREIGN PATENT DOCUMENTS

| | | |
|---|---|---|
| FR | 2902656 | 12/2007 |
| IN | 200500654 I2 | 3/2006 |
| JP | 2003300824 | 10/2003 |

OTHER PUBLICATIONS

"Synergy, Additivism and Antagonism in Immunosuppression," by M.C. Berenbaum. Clin. Esp. Immunol. (1977) 28, 1-18.
Parle et al., "Traditional Medicinal Formulation, Chyawanprash," Indian Journal of Traditional Knowledge vol. 5 (4), 2006, pp. 484-488.
"EnzChek Gelatinase/Collagenase Assay Kit." Molecular Probes Product Information, Revised: Mar. 22, 2001.
"Novel Fluorometric Assay for Hydroxyl Radical Prevention Capacity Using Fluorescein as the Probe." Journal of Agricultural and Food Chemistry, 2002, vol. 50, pp. 2772-2777.
"Development and Validation of an Improved Oxygen Radical Absorbance Capacity Assay Using Fluorescein as the Fluorescent Probe." Journal of Agricultural and Food Chemistry, 2001, vol. 49, pp. 4619-4626.
"Inhibition of Hyaluronidase Adapted from: Enzymatic Assay of Hyaluronidase," by A. Dorfman. Methods in Enzymology, vol. I, pp. 166-173 (1955).
Declaration of Bruce Abedon Regarding Chyawanprash dated Mar. 30, 2011.
Hanif et al., "Antioxidant Factor of Amla Fruit," Pakistan Journal of Scientific Research (1966), 18(1), 61-3.
Khopde et al., "Characterizing the Antioxidant Activity of Amla (Phyllanthus Emblica) Extract," Current Science (2001) vol. 81, No. 2, pp. 185-190.
Banerjee et al., "Preparation, Evaluation and Hair Growth Stimulating Activity of Herbal Hair Oil," Journal of Chemical and Pharmaceutical Research (2009) vol. 1, No. 1, pp. 261-267.
Edeas, "Citrus Bioflavonoids," Phytotherapie, Oct. 2007, vol. 5, No. 4, pp. 210-211.
Restriction Requirement dated Sep. 3, 2010, in related U.S. Appl. No. 12/604,092, titled "Composition of Ashwagandha and Indian Gooseberry."
Response to Restriction Requirement dated Oct. 14, 2010, in related U.S. Appl. No. 12/604,092, titled "Composition of Ashwagandha and Indian Gooseberry."
Office Action dated Dec. 3, 2010, in related U.S. Appl. No. 12/604,092, titled Composition of Ashwagandha and Indian Gooseberry.
Response to Office Action dated Mar. 3, 2011, in related U.S. Appl. No. 12/604,092, titled "Composition of Ashwagandha and Indian Gooseberry."
Office Action dated Apr. 15, 2011 in related U.S. Appl. No. 12/604,092 filed Oct. 22, 2009.
Response to Office Action dated Jul. 15, 2011 in related U.S. Appl. No. 12/604,092 filed Oct. 22, 2009.
Final Office Action dated Aug. 15, 2011 in related U.S. Appl. No. 12/604,092 filed Oct. 22, 2009.
Response to Final Office Action dated Jan. 4, 2012 in related U.S. Appl. No. 12/604,092 filed Oct. 22, 2009.
Request for Continued Examination dated Feb. 15, 2012 in related U.S. Appl. No. 12/604,092 filed Oct. 22, 2009.
Notice of Allowance dated Feb. 28, 2012 in related U.S. Appl. No. 12/604,092 filed Oct. 22, 2009.

(Continued)

*Primary Examiner* — Qiuwen Mi
(74) *Attorney, Agent, or Firm* — Downs Rachlin Martin PLLC

(57) ABSTRACT

Compositions including combinations of β-glucan and *Withania somnifera* for increasing the immune activity of certain target cytokines and phagocytosis, and reducing cortisol or corticosterone. Methods of improving immunity activity under periods of stress including chronic stress with a combination of β-glucan and *Withania somnifera* are also described. Particular combinations of β-glucan and *Withania somnifera* synergistically increases the immune activity of the cytokines IL-12 and IL-6 over expected values.

3 Claims, No Drawings

(56) References Cited

OTHER PUBLICATIONS

Notice of Allowance dated Aug. 8, 2012 in related U.S. Appl. No. 13/532,380 filed Jun. 25, 2012.
Restriction Requirement dated Jun. 25, 2013, in parent U.S. Appl. No. 13/532,338 filed Jun. 25, 2012.
Response to Restriction Requirement dated Jul. 23, 2013, in parent U.S. Appl. No. 13/532,338 filed Jun. 25, 2012.
Notice of Allowance dated Aug. 5, 2013 in parent U.S. Appl. No. 113/532,338 filed Jun. 25, 2012.
Author Kaiyadeya Title of publication—Kaiyadevanighantau Page(s) being submitted—05 (p. 04-08). ( Ref.pg. No. of publication:193 ) Publication Date—Edn. 1st, 1979 Publisher—Chaukhambha Orientalia Place of Publication—Varanasi, India.†
Author Sodhala Title of publication—Gadanigrahah Part-1(Prayoga Khanda) Page(s) being submitted—08 (p. 09-16) ( Ref.pg. No. of publication:309-310 ) Publication Date—Ed. 3rd 1999 Publisher—Chaukhamba Sanskrit Sansthan Place of Publication—Varanasi, India.†
Author—Cakrapanidattah Title of publication—Cakradattah—Translated by Indradeya Tripathi; Chaukhamba Sanskrit Samsthan Page(s) being submitted—08 (p. 17-24) ( Ref.pg. No. of publication:433-434 ) Publication Date—Ed. 4th 2002 Publisher—B. Jain Publishers Place of Publication—Varanasi, India.†

† cited by third party

COMPOSITION OF BETA-GLUCAN AND ASHWAGANDHA

RELATED APPLICATIONS

This application is a divisional of U.S. patent application Ser. No. 13/532,338, filed Jun. 25, 2012, entitled "Composition of Beta-Glucan and Ashwagandha," now allowed, which application claims the benefit of priority of U.S. Provisional Application Ser. No. 61/501,029, filed Jun. 24, 2011 and titled "Composition of Beta-Glucan and Ashwagandha." Each of these applications is incorporated by reference herein in its entirety.

FIELD OF THE INVENTION

The present invention generally relates to the field of botanical based nutraceuticals or dietary supplements related to stress reduction and/or immune support. In particular, the present invention is directed to an improved health composition of β-glucan and ashwagandha.

BACKGROUND

The immune system is the body's protective network that is designed to, among other things, fend off invasion from pathogens such as bacteria, viruses, chemicals, and even to act as a surveillance system against the development of cancer. Under normal circumstances, the immune system is highly efficient, providing multiple defenses to keep the body healthy.

Stress can weaken the immune system and can produce symptoms such as fever, weight loss, musculoskeletal pain, and fatigue. Functions of the immune system suspected to be impaired under stressed conditions include those of the B-lymphocytes (B cells) and T-lymphocytes (T cells), cytokines, as well as those of the phagocytic and complement systems. Chronic stress can raise cortisol levels, which can further weaken the immune system.

SUMMARY OF THE DISCLOSURE

In a first exemplary aspect a therapeutic composition of *Withania somnifera* and β-glucan consists essentially of a therapeutically effective combination of *Withania somnifera* and β-glucan, wherein said *Withania somnifera* and said β-glucan are a therapeutically effective combination for increasing cytokine production within an animal and reducing cortisol or corticosterone within the animal.

In another exemplary aspect a method of improving immune activity within a animal body comprises administering to an animal a therapeutic composition consisting essentially of a therapeutically effective combination of *Withania somnifera* and β-glucan such that the therapeutic composition improves cytokine production and reduces cortisol within the animal.

In yet another exemplary aspect a therapeutic method for improving the immune activity and reducing stress in an animal subject suffering from chronic stress comprises administering a composition consisting essentially of a immune activity improving effective combination of an extract of β-glucan and *Withania somnifera* to a animal in need thereof.

DETAILED DESCRIPTION

An improved health composition is provided that includes a combination of β-glucan and ashwagandha (*Withania somnifera*) for improvement in immune system activity and reduced immune system suppression. In one example, the improved health composition may be capable of being ingested by an animal, including but not limited to, a human animal. In such an example, one or more of the health benefits discussed herein attributable to an improved health composition having β-glucan and ashwagandha may be attainable through the ingestion of the composition by an animal.

Capable of being ingested by a human may include, but is not limited to, the inclusion of an improved health composition of the present disclosure in a beverage (e.g., hot, cold, etc.). Ingestion of an improved health composition of the present disclosure may also be facilitated, for example, by including a combination of β-glucan and ashwagandha as described herein in a nutritional product (e.g., a soup, a vitamin enriched granola bar, a nutritional bar, whole grain bread), a dietary supplement (e.g., a capsule, a tablet, a stick pack, an effervescent, a liquid), a food product (e.g., hot, cold, etc.), a confectionary, an oil, a meal replacement, a cereal, a baked good, a candy, a gum, a lozenge, and any combinations thereof.

β-glucans are sugars that are found in the cell walls of, for example, bacteria, fungi, yeasts, algae, lichens, and plants, such as, but not limited to, oats and barley. Poly-branched β-1,3-(D)-glucans are naturally occurring polysaccharides, with or without β-1,6-(D)-glucose side chains. β-1,3-(D)-glucan with or without β-1,6-glucan linkage extracted from a yeast cell wall (*Saccharomyces cerevisiae*) can act as a potent non-specific immune-activator.

In one example, β-glucan is utilized in a composition as described herein in the form of an extract. Various methods for extracting β-glucan are known to those of ordinary skill. In one example, β-glucan as used in one or more exemplary composition as described herein includes a β-glucan extract prepared according to one or more methodologies set forth in U.S. Pat. No. 5,854,404 to Nanba et al., entitled "Antitumor Substance Extracted From Grifola," the descriptions of which are incorporated herein by reference in their entirety.

Ashwagandha (formally known as *Withania somnifera*) is a plant. In one example, it is utilized in a composition as described herein in the form of an extract. Various methods for extracting botanical extracts are known to those of ordinary skill. In one example, ashwagandha as used in one or more exemplary composition as described herein includes an ashwagandha extract prepared according to one or more methodologies set forth in U.S. Pat. No. 6,713,092 to Ghosal, entitled "*Withania Somnifera* Composition, Method For Obtaining Same And Pharmaceutical, Nutritional And Personal Care Formulations Thereof", the descriptions of which are incorporated herein by reference in their entirety. In another example, an improved health composition includes ashwagandha extract prepared according to one or more of the examples set forth in U.S. Pat. No. 6,713,092 to Ghosal, entitled "*Withania Somnifera* Composition", the descriptions of which are incorporated herein by reference in their entirety. In another example, ashwagandha as used in one or more exemplary compositions as described herein is an ashwagandha extract prepared according to one or more methodologies set forth in U.S. Pat. No. 6,153,198 to Ghosal, entitled "*Withania Somnifera* Composition", the descriptions of which are incorporated herein by reference in their entirety.

In an exemplary composition, an improved health composition of ashwagandha and β-glucan includes a therapeutically effective amount of ashwagandha and β-glucan such that the immune activity exceeds, or at least substantially returns to, non-stressed values and stress induced secretions are returned to non-stressed amounts.

In an example, an improved health composition of β-glucan and an ashwagandha extract is a nutraceutical ingredient for dietary supplement and personal care that improves immune system activity including phagocytosis as well as pleiotropic cytokines that impact both innate and adaptive immunity.

In another example, an improved health composition consists essentially of a synergistically effective composition of about 1 wt. % β-glucan and about 99 wt. % ashwagandha to about 50 wt. % β-glucan and 50 wt. % ashwagandha. This composition achieves one or more of the benefits disclosed herein.

In yet another example, an improved health composition consists essentially of a synergistically effective composition of about 1 wt. % β-glucan and about 99 wt. % ashwagandha to about 15 wt. % β-glucan and about 85 wt. % ashwagandha. This composition achieves one or more of the benefits disclosed herein.

In another example, an improved health composition consists essentially of a synergistically effective composition of about 10.7 wt. % β-glucan and about 89.3 wt. % ashwagandha. This composition achieves one or more of the benefits disclosed herein.

In still another example, an improved health composition consists essentially of a synergistically effective composition of about 5 wt. % β-glucan and about 95 wt. % ashwagandha to about to about 6 wt. % β-glucan about 94 wt. % ashwagandha. This composition achieves one or more of the benefits disclosed herein.

In still yet another example, an improved health composition consists essentially of about 5.6 wt. % β-glucan and about 94.4 wt. % ashwagandha. This composition achieves one or more of the benefits disclosed herein.

In a further example, a method for improving immunity in an animal includes administering an improved health composition consisting essentially of β-glucan and ashwagandha to an animal at a dosage of about 0.2 mg/kg/day of β-glucan to about 7 mg/kg/day of β-glucan in combination with ashwagandha. In this example, weight of the animal in kilograms is determined based upon the weight of the animal that plans to ingest the composition. An animal's weight can be determined at any time during the calendar day. In an example, an animal's weight may be an average of weight measurements taken throughout a calendar day. In such an example, divided doses of the improved health composition may be ingested at some or all of the measurement times. This composition achieves one or more of the benefits disclosed herein.

In yet a further example, an improved health composition consists essentially of about 500 mg/day of β-glucan in combination with an amount of ashwagandha. This composition achieves one or more of the benefits disclosed herein.

As presented in detail below, an exemplary composition of β-glucan and ashwagandha improves the immunity activity of phagocytosis and IFN-γ. Corticosterone (the animal equivalent of human cortisol) production, during periods of stress, is also reduced to about non-stressed levels. Additionally, although ashwagandha and β-glucan individually have limited, if any, impact on the immunity activities of IL-12 under stressed conditions, the combination of β-glucan and ashwagandha increases the amount of IL-12 to well above non-stressed control values.

In an exemplary embodiment, a method of improving the immune activity and reducing stress in an animal includes administering a therapeutically effective amount of a combination consisting essentially of β-glucan and ashwagandha to an animal in a stressed condition so as to improve IL-12 and IL-6 production.

Administration of a therapeutic composition of β-glucan and ashwagandha to achieve the physiological results as described herein may be via any of the accepted modes of administration for systemically active substances to humans or non-human animals. Exemplary methods of administration may include, but are not limited to, oral, parenteral, aerosol, and sustained release systems. Oral dosage forms can encompass, but are not limited to, tablets, capsules, powders, and granules. Unit dosage forms such as tablets and capsules may contain any suitable predetermined amount of a composition of β-glucan and ashwagandha, and may be administered one or more at a time at regular intervals. In one exemplary aspect, a chosen form of administration does not materially affect the beneficial aspects of the composition of β-glucan and ashwagandha as described herein.

Delivery options for a combination of β-glucan and ashwagandha may be any of those known in the pharmaceutical arts which are suitable for the method of administration and dosage required. Such delivery options may include, but are not limited to, tablets, pills, capsules, powders, aerosols, suppositories, skin patches, parenterals, and oral liquids including, but not limited to, oil aqueous suspensions, solutions and emulsions. As another example, delivery options may be sustained release devices.

In an example, oral dosage forms may be provided with suitable coatings which, if desired, may be resistant to gastric juices. In one such example, concentrated sugar solutions may be used, which may include, but are not limited to, gum arabic, talc, polyvinylpyrrolidone, polyethylene glycol, and/or titanium dioxide, lacquer solutions and suitable organic solvents or solvent mixtures, and any combinations of the same. As would be understood by those of ordinary skill, in order to produce coatings resistant to gastric juices, solutions of suitable cellulose preparations such as, but not limited to, acetyl-cellulose phthalate or hydroxypropylmethylcellulose phthalate, dyestuffs and pigments may be added.

Oral dosage forms include, for example, capsules made of gelatin or vegetable origin. In one such example, a capsule can contain the active compounds in the form of granules which may be mixed with fillers (e.g., lactose), binders (e.g., starches), and/or lubricants (e.g., talc or magnesium stearate). A capsule may also include one or more stabilizers. In another such example, when using soft capsules, the active compounds can be dissolved or suspended in suitable liquids, such as, but not limited to, fatty oils, liquid paraffin, or liquid polyethylene glycols. Stabilizers may also be added.

In another example, a rectal administration of the composition can include, but is not limited to, suppositories, which can include a combination of the active compounds with a suppository base. Example suppository bases include, but are not limited to, natural or synthetic triglycerides, paraffin hydrocarbons, polyethylene glycols, or higher alkanols, and any combinations of the same. In addition, it is also possible to use gelatin or vegetable origin rectal capsules which can consist of a combination of the active compounds with a base. Example base materials include, but are not limited to, liquid triglycerides, polyethylene glycols, or paraffin hydrocarbons, and any combinations of the same.

Other dosage forms include, but are not limited to, suitable solutions for administration parenterally or orally, and solutions which can be administered buccally or sublingually. Example formulations for parenteral administration forms include, but are not limited to, aqueous solutions of active compounds in water-soluble or water-dispersible form. In addition, suspensions of the active compounds as oily injection suspensions may be administered. Example lipophilic solvents or vehicles include, but are not limited to, fatty oils (e.g., sesame oil) or synthetic fatty acid esters (e.g., ethyl oleate or triglycerides), and any combinations of the same. Aqueous injection suspensions may contain substances which increase the viscosity of the suspension. Example substances for increasing viscosity include, but not limited to, sodium carboxymethyl cellulose, sorbitol, dextran, or glycerin, and any combinations of the same. Such compositions may also include adjuvants such as preserving, wetting, emulsifying, and dispensing agents.

A composition of β-glucan and ashwagandha as described herein may also be sterilized. In one example, a composition may be filtrated through a bacteria-retaining filter. In another example, a composition can incorporate sterilizing agents into the compositions. In yet another example, a composition may also be manufactured in the form of sterile solid compositions which can be dissolved or suspended in sterile water, saline, or other injectable medium prior to administration.

In addition to the active compounds, i.e., β-glucan and ashwagandha, the pharmaceutical compositions as described herein may contain suitable excipients and auxiliaries which facilitate processing of the active compounds into preparations which can be used pharmaceutically, but do not significantly alter the beneficial effects of the composition.

Suitable excipients are known in the art. For example, an excipient can be a filler. Example fillers include, but are not limited to, a sugar (e.g., lactose or sucrose, mannitol or sorbitol), cellulose preparations and/or calcium phosphates (e.g., tricalcium phosphate, microcrystalline cellulose, or calcium hydrogen phosphate), and any combinations of the same. An excipient can also be a binder. Example binders include, but are not limited to, a starch, a paste, a maize starch, a wheat starch, a rice starch, a potato starch, a gelatin, a gum tragacanth, a methyl cellulose, a hydroxypropylmethylcellulose, a sodium carboxymethylcellulose, a polyvinyl pyrrolidone, and any combinations of the same. An excipient can also be a disintegrating agent. Example disintegrating agents include, but are not limited to, a starch (e.g., a maize starch, a wheat starch, a rice starch, a potato starch, etc.), a croscarmellose sodium, a carboxymethyl starch, a cross-linked polyvinyl pyrrolidone, an agar, or an alginic acid or a salt thereof (e.g., sodium alginate), and any combinations of the same.

Suitable auxiliaries are known in the art. For example, auxiliaries can be, but are not limited to, flow-regulating agents and lubricants (e.g., a silica, a talc, a stearic acid, and any combinations of the same), or a salt thereof (e.g., a magnesium stearate or a calcium stearate), a polyethylene glycol, and any combinations of the same.

Example 1

An example improved health composition was prepared using:
β-glucan
Ashwagandha
in a ratio of about 3:50 weight to weight (w:w).

An embodiment of the composition of β-glucan and ashwagandha was tested utilizing in vitro mouse models whereby a non-stress control group and a stress group were treated orally twice a day, with a combination of an extract of β-glucan and an extract of ashwagandha, for two weeks. The control group and the stress group were subdivided into 4 different treatment groups: negative control (PBS), β-glucan, ashwagandha, and β-glucan and ashwagandha in combination.

Five different immune activities were assessed: phagocytosis, corticosterone, interleukin (IL)-6, IL-12, and interferon (IFN)-γ. Phagocytosis is the cellular process of engulfing solid particles by a cell with its cell membrane to form an internal phagosome. Bacteria, dead tissue cells, and small mineral particles are all examples of objects that may be phagocytosed. Phagocytosis is expected to decrease under periods of stress. In an example, an improved composition of β-glucan and ashwagandha increased phagocytosis under stressed and non-stressed conditions.

Corticosterone is the mouse corticosteroid equivalent of human cortisol. The secretion of corticosterone in mice occurs in response to stress, and has been found to be responsible for several stress-related changes in the body. Specifically, increases in corticosterone have been shown to have effects such as, but not limited to, suppressed thyroid function, blood sugar imbalances such as hyperglycemia, decreased bone density, decrease in muscle tissue, higher blood pressure, lowered immunity and inflammatory responses in the body, slowed wound healing, and other health consequences. In an example, an improved composition of β-glucan and ashwagandha decreased corticosterone production under stressed conditions, returning corticosterone to approximately non-stressed conditions.

IL-6 is an interleukin that acts as both a pro-inflammatory and anti-inflammatory cytokine. It is secreted by T cells and macrophages to stimulate immune response to trauma. In terms of host response to a foreign pathogen, IL-6 improves resistance against the pathogen. IL-6 is an important moderator of fever and of acute phase response. It is capable of crossing the blood brain barrier and changing the body's temperature setpoint. IL-6 can be secreted by macrophages in response to specific microbial molecules, which bind to a group of detection molecules of the innate immune system. These detection molecules are present on the cell surface and intracellular compartments and induce intracellular signaling cascades that give rise to inflammatory cytokine production. In an example, an improved composition of β-glucan and ashwagandha increased IL-6 production under stressed and non-stressed conditions.

IL-12 is an interleukin that is naturally produced by dendritic cells, macrophages, and human B-lymphoblastoid cells in response to antigenic stimulation. IL-12 can stimulate the growth and function of T cells and the production of interferon-gamma (IFN-γ) and tumor necrosis factor-alpha (TNF-α) from T cells and natural killer (NK) cells. In an example, an improved composition of β-glucan and ashwagandha increased IL-12 production under stressed and non-stressed conditions.

IFN-γ is produced by activated macrophages and is considered an important mediator of acute inflammation in response to Gram-negative bacteria and other infectious microbes. In an example, an improved composition of β-glucan and ashwagandha increased IFN-γ production during stressed conditions to values found under non-stressed conditions.

| EXPERIMENTAL GROUPS TABLE | |
| --- | --- |
| B-glucan | 30.75 ug |
| Ashwagandha | 512.5 ug |
| B-glucan + Ashwagandha | 30.75 ug + 512.5 ug |
| Control (PBS) | 500 ug |

Treatment groups of female Balb/c mice were force-fed corresponding respective treatments detailed in the Experimental Groups Table above twice per day for two weeks. During this time interval, some of the mice in each respective treatment group were subjected to cold stress by incubation for 60 minutes at 4° C. per day. Phagocytosis was tested using peripheral blood cells incubated with 0.05 ml of 2-hydroxyethyl methacrylate particles (HEMA; 5×10$^8$/ml). The experiment used HEMA, because their use, dose, and timing are well established in studies. The test tubes were incubated at 37° C. for 60 minutes, with intermittent shaking. Smears were stained with Wright stain (Sigma). The cells with three or more HEMA particles were considered positive. Higher levels of phagocytosis indicate improved immune response in the test subject.

Serum corticosterone was measured by the following assay: on day 14, blood samples were collected by venipucture from mice under pentobarbital anesthesia. Obtained sera was collected and stored at −80° C. before assay. Serum corticosterone was measured using an ELISA kit (Diagnostics Systems Lab, TX) according to the manufacturer's instructions. Lower corticosterone levels indicate lower stress levels in the subject.

Cytokine production, e.g., IL-6, IL-12, and IFN-γ, was measured by the following technique: Purified spleen cells from the tested mice (2×10$^6$/ml in RPMI 1640 medium with 5% FCS) were added into wells of a 24-well tissue culture plate. After addition of 1 μg of Concanavalin A (Sigma), cells were incubated for 48 hrs. in a humidified incubator (37° C., 5% CO$_2$). At the endpoint of incubation, supernatants were collected, filtered through 0.45 μm filters and tested for the presence of IL-6, IL-12 and IFN-γ. Levels of individual cytokines were measured using a Quantikine mouse IL-6, IL-12 or IFN-γ kit, respectively (R&D Systems, Minneapolis, Minn.). Higher levels of cytokines indicate improved immune system capabilities in the subject.

Table 1, below, shows the effect on immune activities of ashwagandha when compared to the control, PBS, under non-stressed conditions. Table 1 includes columns detailing the immune activities for the control, PBS, and the ashwagandha administered mice under non-stressed conditions. As is evident from the results of this experiment, for all immune activities the change was negligible.

TABLE 1

Ashwagandha Effect on Non-Stressed Mice

| Measurement | PBS Non-Stressed | Ashwagandha Non-Stressed |
|---|---|---|
| Phagocytosis | 28.3 | 29.1 |
| Corticosterone | 126.8 | 119.5 |
| IL-6 | 7.9 | 8.1 |
| IL-12 | 7.9 | 11.1 |
| IFN-γ | 92.3 | 111 |

Table 2, below, shows the effect on immune activities of ashwagandha when compared to the control, PBS, under stressed conditions. Table 2 includes columns detailing the immune activities for PBS administered mice and the ashwagandha administered mice under stressed conditions. Comparing Tables 1 and 2, under stressed conditions, the PBS administered mice experienced a decrease in phagocytosis, IL-6, IL-12, and IFN-γ production, with IL-6, IL12, and IFN-γ production showing sharp declines. When the PBS mice are compared to those administered with ashwagandha, phagocytosis, IL-6, IL-12, and IFN-γ immunity activities returned to about PBS levels, but with the amount of corticosterone remaining above the control value.

Comparing the mice administered ashwagandha under non-stressed and stressed conditions reveals a mixed result. Administration with ashwagandha under stressed conditions appears to increase the immune activity for IL-6 and IL-12 to non-stressed condition values.

TABLE 2

Ashwagandha Effect on Stressed Mice

| Measurement | PBS Stressed | Ashwagandha Stressed |
|---|---|---|
| Phagocytosis | 21.8 | 30.7 |
| Corticosterone | 214.5 | 150.3 |
| IL-6 | 1.1 | 10.3 |
| IL-12 | 1.5 | 15.5 |
| IFN-γ | 36.9 | 88.1 |

Table 3, below, shows the effect on immune activities of an extract of β-glucan when compared to the mice administered the control, PBS, under non-stressed conditions. Table 3 includes columns detailing the immune activities for the PBS administered mice and the β-glucan administered mice under non-stressed conditions. β-glucan has a positive effect on phagocytosis and IL-6 production in non-stressed mice, but has limited effectiveness on reducing corticosterone or increasing IL-12 or IFN-γ cytokines.

TABLE 3

β-glucan Effect on Non-Stressed Mice

| Measurement | PBS Non-Stressed | β-glucan Non-Stressed |
|---|---|---|
| Phagocytosis | 28.3 | 39.9 |
| Corticosterone | 126.8 | 127.1 |
| IL-6 | 7.9 | 36.9 |
| IL-12 | 7.9 | 12.9 |
| IFN-γ | 92.3 | 98.6 |

Table 4, below, shows the effect on immune activities of β-glucan administered mice when compared to the control, PBS, under stressed conditions. Table 4 includes columns detailing the immune activities for the PBS administered mice and the β-glucan administered mice under stressed conditions. As presented above, the PBS mice experienced a decrease in phagocytosis, IL-6, IL-12, and IFN-γ production, with IL-6, IL12, and IFN-γ production showing sharp declines. When the PBS mice are compared to those administered β-glucan, phagocytosis, IL-6, and IL-12 immunity activities returned to non-stressed conditions. Notably, treatment with β-glucan has little effect on corticosterone levels in stressed mice and does not return IFN-γ to non-stress condition values.

Comparing the mice administered β-glucan under non-stressed and stressed conditions, reveals that under stressed conditions administration with β-glucan only returns the amount of phagocytosis to about its original non-stressed value.

TABLE 4

β-glucan Effect on Stressed Mice

| Measurement | PBS Stressed | β-glucan Stressed |
|---|---|---|
| Phagocytosis | 21.8 | 37.1 |
| Corticosterone | 214.5 | 178.1 |

TABLE 4-continued

β-glucan Effect on Stressed Mice

| Measurement | PBS Stressed | β-glucan Stressed |
|---|---|---|
| IL-6 | 1.1 | 16.9 |
| IL-12 | 1.5 | 8.8 |
| IFN-γ | 36.9 | 64.8 |

Table 5, below, shows the effect on immune activities of an exemplary embodiment of the combination of β-glucan and ashwagandha as described above when compared to the mice administered the control, PBS, under non-stressed conditions. As with the β-glucan only treatment group, the β-glucan used for this experiment was from an extract of maitake mushrooms. Table 5 includes columns detailing the immune activities for the PBS administered mice and the combination administered mice under non-stressed conditions. In general, the combination has a positive effect on phagocytosis, IL-6, and IL-12 production in non-stressed mice, but has limited effectiveness on corticosterone or IFN-γ.

TABLE 5

Combination Effect on Non-Stressed Mice

| Measurement | PBS Non-Stressed | Combination Non-Stressed |
|---|---|---|
| Phagocytosis | 28.3 | 40.1 |
| Corticosterone | 126.8 | 120.8 |
| IL-6 | 7.9 | 33.5 |
| IL-12 | 7.9 | 17.8 |
| IFN-γ | 92.3 | 115.4 |

Table 6, below, shows the effect on immune activities of an exemplary embodiment of the combination of β-glucan and ashwagandha as described above when compared to the mice administered the control, PBS, under stressed conditions. Table 6 includes columns detailing the immune activities for the PBS administered mice and the combination administered mice under stressed conditions. As presented before, the PBS mice experienced a decrease in phagocytosis, IL-6, IL-12, and IFN-γ production, with IL-6, IL12, and IFN-γ production showing sharp declines. When the PBS mice are compared to those administered with the combination of β-glucan and ashwagandha, phagocytosis, IL-6, and IL-12 immunity activities returned to well above non-stressed control values, with the amount of corticosterone and IFN-γ returning to about control levels.

Comparing the mice administered the combination under non-stressed and stressed conditions, reveals that under stressed conditions, administration with the combination returns phagocytosis, corticosterone, and IFN-γ to near their respective non-stressed combination values and surpasses the non-stressed values for IL-6 and IL-12.

TABLE 6

Combination Effect on Stressed Mice

| Measurement | PBS Stressed | Combination Stressed |
|---|---|---|
| Phagocytosis | 21.8 | 42.9 |
| Corticosterone | 214.5 | 133.8 |
| IL-6 | 1.1 | 44.9 |
| IL-12 | 1.5 | 26.8 |
| IFN-γ | 36.9 | 95.9 |

From the data presented above it is apparent that an exemplary combination of β-glucan and ashwagandha has a synergistic effect on the production of IL-12. Specifically, under stressed conditions, β-glucan and ashwagandha individually return IL-12 to about normal levels and neither have a significant effect on IL-12 under non-stressed conditions. However, when provided in combination, IL-12 production is improved under non-stressed conditions and more unexpectedly, is vastly improved under stressed conditions when compared to the administration of the combination under non-stressed conditions or β-glucan and ashwagandha individually.

The data in this example also shows a synergistic effect with respect to IL-6 production. IL-6 production was unaffected by ashwagandha alone under non-stressed conditions. IL-6 production increased under stressed conditions when ashwagandha alone was administered, but only returned to non-stressed condition values. Under non-stressed conditions, IL-6 production increased dramatically when β-glucan alone was administered. Yet, under stressed conditions, IL-6 production decreased by more than 50% when β-glucan alone was administered. The combination of β-glucan and ashwagandha showed a significant increase in IL-6 production under non-stressed conditions, which would be consistent with the effect seen by administration of β-glucan alone. However, while one would expect a decrease of IL-6 production from non-stressed values when the subject is under stress because of the significant drop seen in the effect of β-glucan alone, the data reveals that IL-6 production increased substantially above non-stressed levels when the combination of β-glucan and ashwagandha was administered.

It is understood that all embodiments using the term "about" in conjunction with a certain amount or range of amounts, are intended to include the phrase "not about" in conjunction with the certain amount or range of amounts.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A therapeutic composition of *Withania somnifera* and β-glucan consisting essentially of a therapeutically effective combination of *Withania somnifera* and β-glucan, wherein said *Withania somnifera* and said β-glucan are a therapeutically effective combination for increasing cytokine production within an animal and reducing cortisol or corticosterone within the animal, further wherein said *Withania somnifera* and said β-glucan are present in said composition in a weight ratio of about 5.6:94.4 β-glucan to *Withania somnifera*.

2. A therapeutic composition according to claim 1, wherein said cytokines include a cytokine selected from the group consisting of IL-6, IL-12, and IFN-γ, and any combinations thereof.

3. A therapeutic composition according to claim 1, wherein said composition increases phagocytosis.

\* \* \* \* \*